(12) United States Patent
Jacobson et al.

(10) Patent No.: US 7,422,669 B2
(45) Date of Patent: Sep. 9, 2008

(54) MICROFLUIDIC DEVICE AND METHOD FOR FOCUSING, SEGMENTING, AND DISPENSING OF A FLUID STREAM

(75) Inventors: Stephen C. Jacobson, Knoxville, TN (US); J. Michael Ramsey, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 860 days.

(21) Appl. No.: 10/758,718

(22) Filed: Jan. 16, 2004

(65) Prior Publication Data

US 2004/0144648 A1    Jul. 29, 2004

Related U.S. Application Data

(63) Continuation of application No. 09/759,590, filed on Jan. 12, 2001, now Pat. No. 6,790,328.

(60) Provisional application No. 60/175,684, filed on Jan. 12, 2000.

(51) Int. Cl.
*G01N 27/447* (2006.01)
*G01N 27/453* (2006.01)
*B01L 3/02* (2006.01)

(52) U.S. Cl. .................. 204/451; 204/601; 422/100
(58) Field of Classification Search ......... 204/600–605, 204/450–455; 422/99, 100
See application file for complete search history.

(56) References Cited

U.S. PATENT DOCUMENTS

| | | |
|---|---|---|
| 4,908,112 A | 3/1990 | Pace |
| 5,073,239 A | 12/1991 | Hjerten |
| 5,092,973 A | 3/1992 | Zare et al. |
| 5,110,431 A | 5/1992 | Moring |
| 5,116,471 A | 5/1992 | Chien et al. |

(Continued)

FOREIGN PATENT DOCUMENTS

EP    0356160    2/1990

(Continued)

OTHER PUBLICATIONS

C.L. Rice et al., "Electrokinetic Flow in a Narrow Cylindrical Capillary", The Journal of Physical Chemistry, vol. 69, No. 11, Nov. 1965.

(Continued)

*Primary Examiner*—Alex Noguerola
(74) *Attorney, Agent, or Firm*—Dann, Dorfman, Herrell and Skillman, P.C.

(57) ABSTRACT

A microfluidic device and method for forming and dispensing minute volume segments of a material are described. In accordance with the present invention, a microfluidic device and method are provided for spatially confining the material in a focusing element. The device is also adapted for segmenting the confined material into minute volume segments, and dispensing a volume segment to a waste or collection channel. The device further includes means for driving the respective streams of sample and focusing fluids through respective channels into a chamber, such that the focusing fluid streams spatially confine the sample material. The device may also include additional means for driving a minute volume segment of the spatially confined sample material into a collection channel in fluid communication with the waste reservoir.

19 Claims, 5 Drawing Sheets

U.S. PATENT DOCUMENTS

| | | |
|---|---|---|
| 5,126,022 A | 6/1992 | Soane et al. |
| 5,132,012 A | 7/1992 | Miura et al. |
| 5,141,621 A | 8/1992 | Zare et al. |
| 5,180,480 A | 1/1993 | Manz |
| 5,250,263 A | 10/1993 | Manz |
| 5,296,114 A | 3/1994 | Manz |
| 5,328,578 A | 7/1994 | Gordon |
| 5,376,252 A | 12/1994 | Ekstrom et al. |
| 5,480,614 A | 1/1996 | Kamahori |
| 5,498,392 A | 3/1996 | Wilding et al. |
| 5,603,351 A | 2/1997 | Cherukuri et al. |
| 5,630,924 A | 5/1997 | Fuchs et al. |
| 5,705,813 A | 1/1998 | Apffel et al. |
| 5,733,442 A | 3/1998 | Shukla |
| 5,750,015 A | 5/1998 | Soane et al. |
| 5,785,831 A | 7/1998 | Bek |
| 5,858,187 A | 1/1999 | Ramsey et al. |
| 5,858,195 A | 1/1999 | Ramsey |
| 5,872,010 A | 2/1999 | Karger et al. |
| 5,882,496 A | 3/1999 | Northrup et al. |
| 5,888,390 A | 3/1999 | Craig |
| 6,120,666 A | 9/2000 | Jacobson et al. |
| 6,506,609 B1 | 1/2003 | Wada et al. |
| 6,790,328 B2 * | 9/2004 | Jacobson et al. ............ 204/453 |

FOREIGN PATENT DOCUMENTS

| | | |
|---|---|---|
| EP | 0620432 | 10/1994 |
| GB | 2191110 | 12/1987 |
| WO | WO 9810267 | 3/1998 |

OTHER PUBLICATIONS

D.C. Duffy et al., "Rapid Prototyping of Microfluidic Systems in Poly(dimethylsiloxane)", Analytical Chemistry, vol. 70, No. 23, Dec. 1, 1998.

T.L. Hoopman et al., "Microchanneled Structures", Microstructures, Sensors, and Actuators, The American Soc. of Mechanical Engineers, DSC vol. 19, © 1990.

D.J. Harrison et al., "Micromachining a Miniaturized Capillary Electrophoresis-Based Chemical Analysis System on a Chip", Science, vol. 261, Aug. 13, 1993.

G. Blankenstein et al., "Flow Switch for Analyte Injection and Cell/Particle Sorting", Analytical Methods & Instrumentations, Special Issue µTAS, 1996.

* cited by examiner

MICROFLUIDIC DEVICE AND METHOD FOR FOCUSING, SEGMENTING, AND DISPENSING OF A FLUID STREAM

CLAIM FOR BENEFIT OF PRIORITY

This application is a continuation of nonprovisional application No. 09/759,590, filed Jan. 12, 2001, now U.S. Pat. No. 6,790,328, which claims the benefit of priority of provisional application No. 60/175,684 filed Jan. 12, 2000, the entirety of which is incorporated herein by reference.

GOVERNMENT RIGHTS STATEMENT

The U.S. Government has a paid-up license in this invention and the right in limited circumstances to require the patent owner to license others on reasonable terms as provided for by the terms of contract No. DE-AC05-00OR22725 awarded by the U.S. Department of Energy.

FIELD OF THE INVENTION

This invention relates to microfluidic devices for the electrokinetic manipulation of fluidic chemical and biological materials. More specifically, this invention provides a microchip device for spatially confining and dispensing a sample material stream in a manner which lowers the axial extent of the dispensed plug.

BACKGROUND OF THE INVENTION

In order to facilitate the development of the biological and chemical sciences, fluidic microchip technologies are increasingly utilized to perform traditional chemical laboratory functions within a controlled microfabricated environment. Microfabricated chemical instrumentation, also known as "lab-on-a-chip" technology, requires the development of a plurality of microfabricated functional elements or unit processes cooperatively linked on the microchip to perform small volume chemical and biochemical measurements.

These "on-chip" laboratories facilitate the precise transport and analysis of fluidic chemical and biological materials. The known microfluidic devices provide the advantages of reduced analysis time and reagent consumption, ease of automation, and valveless fluid control of nanoliter to sub-nanoliter volumes. A variety of electrically driven separations have been performed within microchannel networks. Microchips have also been developed for controlling chemical reactions, including arrays for solid-phase chemistry, reaction wells for polymerase chain reactions, channels with immobilized enzymes for flow injection analysis, and manifolds for homogenous enzyme assays.

The ability to design and machine channel manifolds with low-volume connections renders microchips suitable for performing several steps of an analytical process on a single device. Microchips that perform multiple chemical reactions with the speed of microscale CE analysis have been fabricated for pre- and post-separation reactions, for DNA restriction digests with fragment sizing, and for cell lysis, multiplex PCR amplification and electrophoretic sizing.

Electrokinetic techniques, i.e., electroosmotically induced fluid transport and/or electrophoretic migration of ions, are the preferred methods of manipulating biological and chemical materials on microfluidic devices. The mixing of two or more liquid-phase materials or the dispensing of a reagent material on a microchip is accomplished by controlling the electric potentials applied to the various reservoirs to electrokinetically drive the materials contained therein through the channels of the microchip. Electrophoresis transports charged species, whereas electroosmosis imparts a velocity to all ions and neutral species. Under conditions where both electroosmosis and electrophoresis are operative, the net velocity of an ion will be the vector sum of the electroosmotic and electrophoretic velocities.

Electrokinetic transport mechanisms are highly effective for effectuating a number of highly useful experiments as identified above. Several applications require the ability to spatially confine a sample material stream with consistent reproducibility. This spatial confinement or "electrokinetic focusing" refers to the use of electrokinetic transport to confine spatially the transport of both fluids and ions. An example of such focusing is disclosed in related U.S. Pat. No. 5,858,187, issued on Jan. 12, 1999, which describes and shows a microfluidic device and method for spatially confining a stream of fluidic material.

Further applications require the ability to dispense a volume segment of a sample material with consistent reproducibility. An example of such dispensing is disclosed in U.S. Pat. No. 5,858,195, granted Jan. 12, 1999, which describes and shows a microfluidic device and method for dispensing a volume segment of a sample material. The entire disclosure of said U.S. Pat. No. 5,858,195 is incorporated herein by reference.

More recently, a need has arisen for an improved microchip wherein the profile of the dispensed segment may be controlled to dispense more minute quantities. Examples of the benefit of shorter axial extent material segments include (i) decreasing the length required for a separation and reducing the analysis time, (ii) enabling faster axial mixing by diffusion of the segment with adjacent materials, and (iii) increasing the number of material segments per unit axial length of channel.

SUMMARY OF THE INVENTION

In accordance with the present invention there is provided a fluidic microchip that is adapted for the spatial confinement of an electrokinetically driven fluidic material stream to permit dispensing of a low profile volume segment of the fluidic material. The apparatus includes a focusing element and a sample channel formed in the surface of a substrate for carrying a sample fluid stream therethrough. The device also includes a focusing channel for carrying a focusing fluid stream therethrough. In addition, the device includes a sample-waste channel for carrying a focused stream of the sample fluid stream therethrough. Further, the device includes a buffer channel for carrying a buffer fluid stream therethrough. Still further, the device includes a collection channel for carrying a volume segment of the focused stream of the sample fluid therethrough.

The sample channel, focusing channel, collection channel, buffer channel, and sample-waste channel have respective first ends in fluid communication with a source of sample fluid, a source of focusing fluid, a source of buffer fluid, a reservoir for sample waste fluid, and a reservoir for a volume segment of the sample fluid stream, respectively. The sample, focusing, buffer, sample-waste, and collection channels have their respective second ends in fluid communication with a chamber.

The buffer, sample, sample-waste, and collection channels intersect directly to form a valving element. The buffer channel and collection channel are formed such that they are positioned opposite to each other across the valving element. The focusing channel intersects the sample channel ahead of and adjacent to the valving element. The focusing channel is formed such that it is positioned more proximal to the sample fluid source than either the buffer channel or collection channel.

The apparatus may include electromotive means operatively connected to the sample fluid and the focusing fluid for (i) electrokinetically driving their respective streams of the sample and focusing fluids through their respective channels into said focusing element such that the focusing fluid stream spatially confines the sample fluid stream within the chamber and (ii) electrokinetically driving the stream of the buffer fluid through the respective channel into said valving element chamber such that a volume segment of the focused sample stream is dispensed into and transported along the collection channel.

In accordance with a second aspect of this invention, there is provided a method for dispensing minute volume segments of the focused sample stream. The method includes the step of conducting a stream of a sample fluid through a sample fluid channel to a focusing element. In the conducting step the width of the sample fluid stream is narrowed in the focusing chamber by transporting a focusing fluid into the focusing element on one side or two opposite sides of the sample fluid stream. The method includes the further step of withdrawing a portion of the focused sample stream from the focusing chamber into the respective sample and sample-waste channels. A stream of buffer fluid is conducted through a buffer channel into the valving element such that a volume segment of the focused sample stream is dispensed into and transported along the collection channel.

Here and throughout this application, the term "chamber" is used to describe an area or zone that includes a "focusing element" and a "valving element" as those terms are described herein.

An alternative to electrokinetic transport mechanisms, the moving of the sample and buffer materials, and any other materials used in a device or method according to the present invention can be accomplished by application of pressure or vacuum to the appropriate channel or channels. It is also contemplated that combinations of electrokinetic, pressure, and/or vacuum transport mechanisms can be utilized in implementing a given device or method in accordance with this invention if desired.

BRIEF DESCRIPTION OF THE DRAWINGS

The foregoing summary, and the following detailed description, will be better understood when read in conjunction with the attached drawings, in which.

DETAILED DESCRIPTION

The fluidic microchip according to this invention will be described in connection with two preferred embodiments thereof. In one embodiment, a focusing element is provided on the microchip in which a sample material stream is laterally confined or focused using a single focusing fluid stream provided through a first focusing channel. In the second embodiment, the microchip according to this invention includes a second focusing channel for providing a second focusing fluid stream operating in conjunction with the first focusing fluid stream for laterally confining or focusing the sample material stream. In both the first and second embodiments, the microchip according to this invention provides a collection channel for receiving a volume segment of the focused sample stream, wherein the volume segment of the focused sample stream is generated by transporting a buffer fluid from a buffer channel through the valving element and into a collection channel.

A device embodying this invention preferably uses electrokinetic forces to drive streams of fluidic materials through the microfabricated channels. The microfabricated device includes a sample channel and one or two focusing channels in fluid communication with a focusing element for spatially confining the streams of fluidic materials traveling therethrough. The microfabricated device further includes buffer and collection channels in fluid communication with the valving element for confining, segmenting, and transporting volume segments of the confined stream of sample fluidic material. The combination of the focusing element and the valving element defines a chamber within which the focusing and dispensing functions take place.

The sample and focusing fluid streams are manipulated such that the sample fluid stream can be narrowed to a desired width. Focusing of the sample fluid stream is preferably achieved using electrokinetic techniques such as electrophoresis, electroosmosis, or a combination thereof. The focusing or spatial confinement is achieved by using a fluidic buffer material that is transported to the focusing element through the focusing channels. The spatial confinement of the sample fluid stream passing through the focusing element is caused by having confluent flow of the focusing fluid with the sample fluid.

Figure 1A:
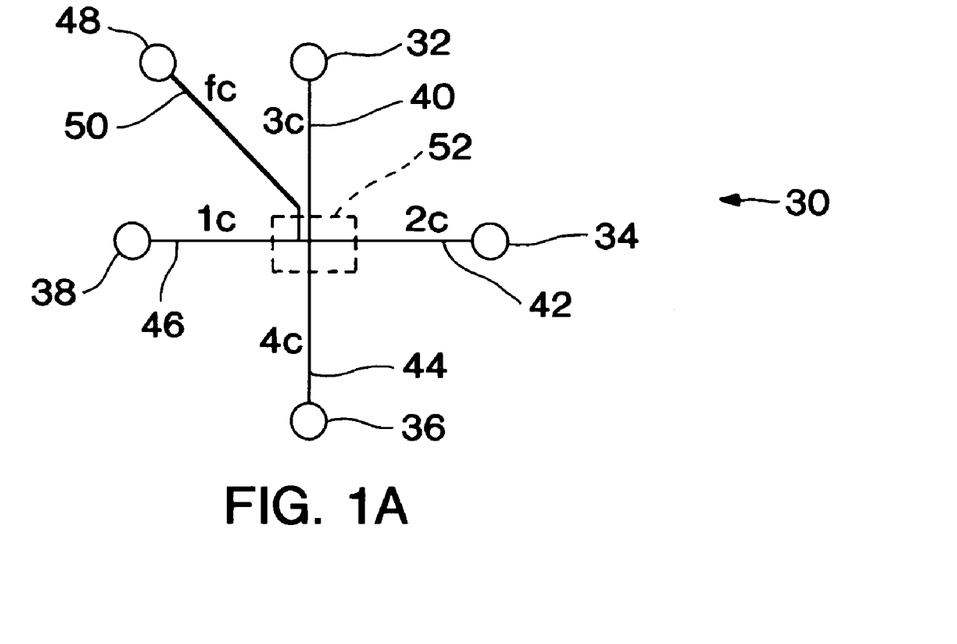
FIG. 1A is a schematic diagram of a fluidic microchip channel network for spatially focusing sample material streams in accordance with a first embodiment of the present invention.
Figure 2A:
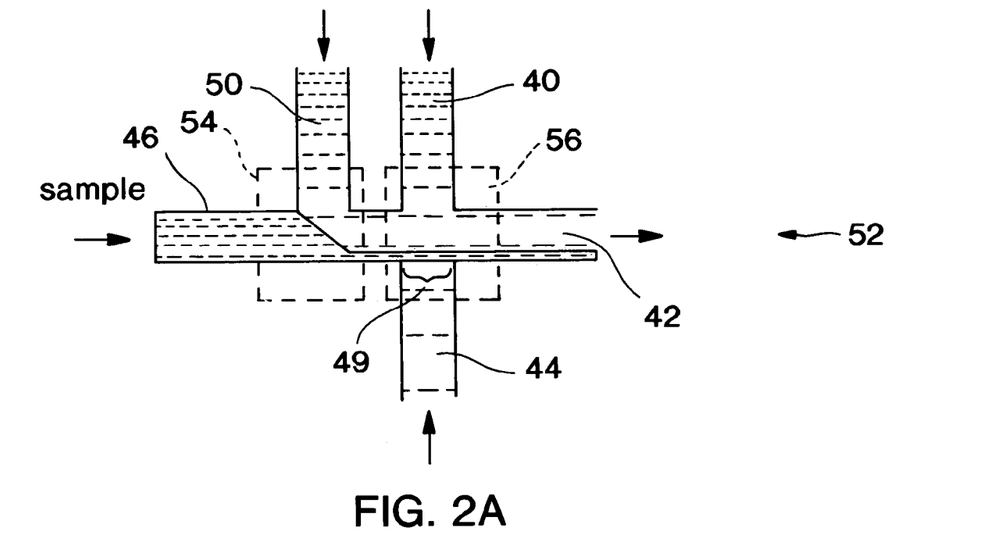
FIGS. 2A and 2B are enlarged views of the chamber of the fluidic microchip device shown in FIG. 1A.

Referring now to the drawings, and in particular to FIGS. 1A and 2A, there is shown schematically a fluidic microchip device 30 in accordance with the present invention. Fluidic microchip device 30 is designed and fabricated from a solid substrate material, preferably glass. Silicon may also be used because of the well-developed technology permitting its precise and efficient fabrication. Other materials, including polymers, quartz, fused silica, sapphire, or plastics are also suitable as substrate materials. The surface of the fluidic microchip device 30 is covered and sealed by a cover plate in a known manner as disclosed in U.S. Pat. No. 5,858,187, the entirety of which is incorporated herein by reference.

The fluid conduction channels on fluidic microchip device 30 are formed using micromachining methods known to those skilled in the art. The micromachining methods available include film deposition processes such as spin coating, chemical vapor deposition, laser fabrication, photolithographic techniques such as UV or X-ray processes, or etching methods which may be performed by either wet chemical processes or plasma processes. Preferably, the microchannel configurations are transferred onto the substrate material using a positive photoresist, photomask, and UV exposure. The channels are etched into the substrate in a dilute, stirred HF/NH$_4$F bath.

The fluidic microchip device 30 has a sample channel 46, a focusing channel 50, a buffer channel 40, a sample-waste channel 42 and a collection channel 44 formed in the surface thereof, which intersect at common ends to form a chamber 52 which is defined by a focusing element 54 and a valving element 56. The focusing channel 50 intersects with the sample channel 46 to form the focusing element 54. The sample channel 46, sample-waste channel 42, buffer channel 40, and collection channel 44 intersect to form the valving element 56. Sample reservoir 38 is formed or positioned at the end of the sample channel 46, such that the sample channel 46 is in fluid communication with the reservoir 38. Focusing reservoir 48, buffer reservoir 32, sample-waste reservoir 34, and waste reservoir 36 are similarly associated with the focusing channel 50, buffer channel 40, sample-waste channel 42, and collection channel 44, respectively.

Figure 4:
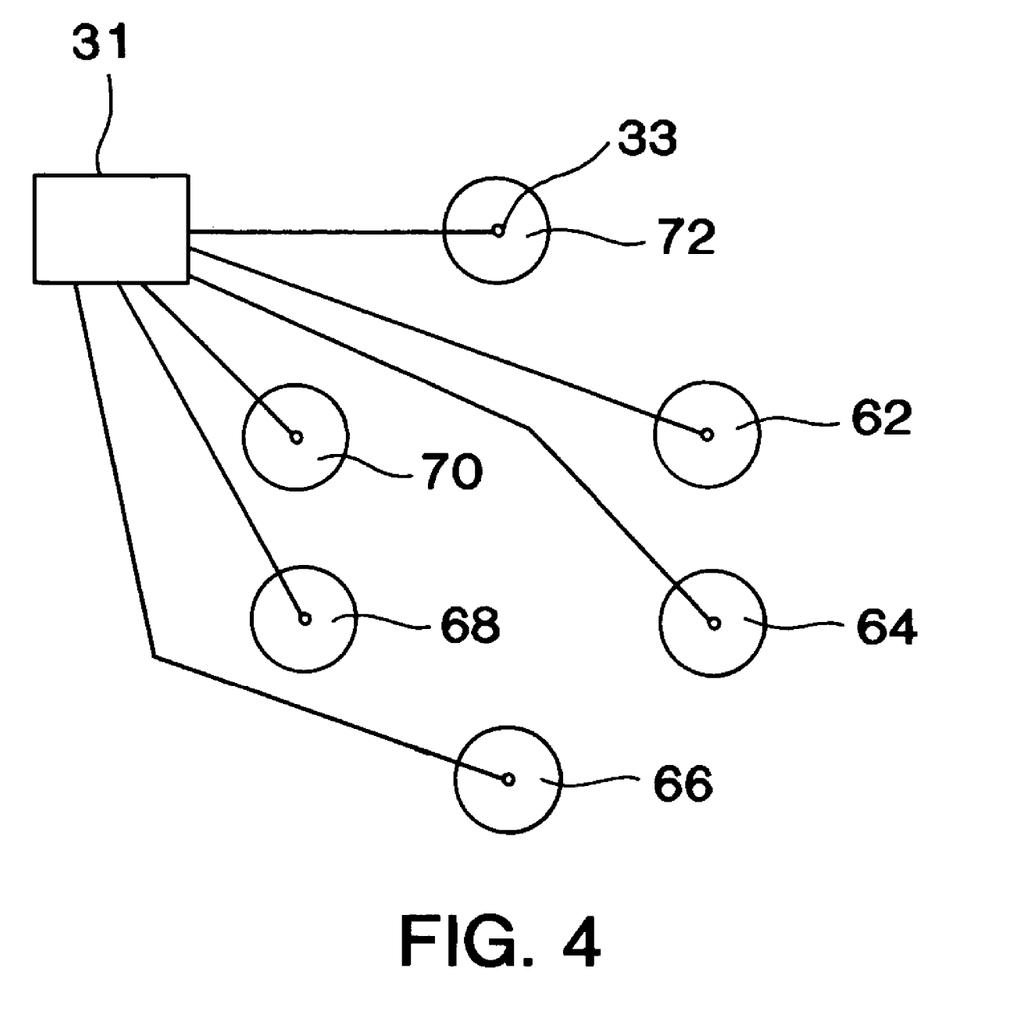
FIG. 4 is a schematic view showing electrical connections between various reservoirs of the microchip and a voltage source.

An electric voltage source 31 is connected to the various reservoirs through platinum wires 33 that extend into the reservoirs as shown in FIG. 4. Electrical contact to the reservoirs is made using platinum wire to operably link the fluidic microchip device 30 with the source of electric potential.

In the operation of the fluidic microchip device 30 in FIG. 1A and 2A, the sample fluid is infused through the focusing element 54 of chamber 52. The electric potentials at the reservoirs are adjusted to increase or diminish the degree of lateral focusing. The potentials applied at the sample and focusing reservoirs 38 and 48 are controlled independently, and the sample-waste reservoir 34 is preferably grounded. Small variations in channel lengths and widths may require that the voltages applied to the reservoirs differ slightly for balancing the field strengths to obtain a symmetric fluid transport in the focusing chamber 52. Assuming that the operational conditions, e.g., relative conductivities of the buffers, applied voltages, electroosmotic transport, remain unchanged, the stream width over time remains essentially constant.

Lateral spatial confinement (focusing) of the sample material stream from sample channel 46 occurs with the transport of focusing fluid into the focusing element 54 from the focusing channel 50 and the transport of sample fluid into focusing chamber 52 from sample channel 46. If the focusing fluid flow is too large, the sample is not electrokinetically transported from the sample reservoir 38 to the focusing chamber 52. In FIG. 2A, arrows depict flow directions in the various channels during focusing.

Figure 2B:
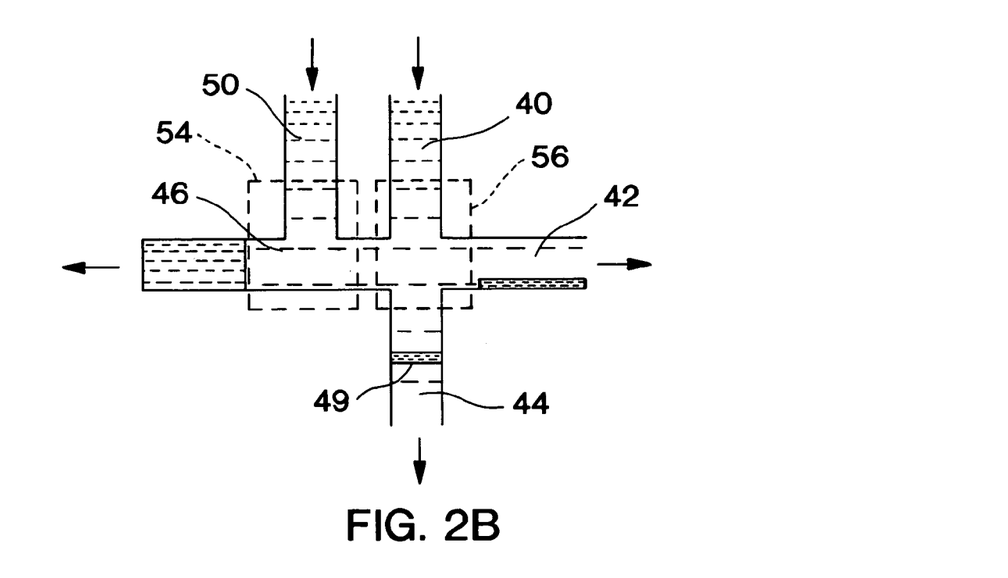

Dispensing of the focused sample material stream from chamber 52 is shown in FIG. 2B. Dispensing begins with the application of electric potentials at the sample reservoir 38, focusing reservoir 48, and the sample-waste reservoir 34 such that the sample fluid is transported from the sample channel 46 and the sample-waste channel 42 towards reservoirs 38 and 34, respectively. Simultaneously, or nearly simultaneously, electric potentials are applied to the buffer reservoir 32 and waste reservoir 36 causing the buffer fluid from the buffer reservoir 32 to flow through the buffer channel 40 and into the collection channel 44. A portion of the segment 49 of the focused sample stream that is present in the intersection between buffer channel 40 and collection channel 44 is transported into collection channel 44 by movement of the buffer fluid. In FIG. 2B, arrows depict flow directions in the various channels during dispensing.

Figure 3A:
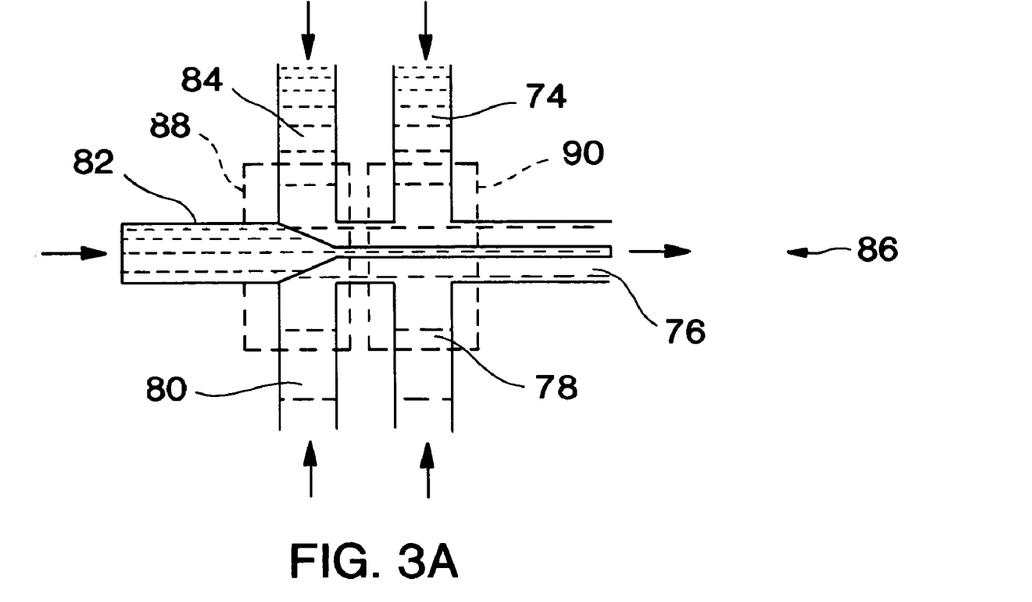
FIGS. 3A and 3B are enlarged views of the chamber of the fluidic microchip device shown in FIG. 1B.

A second preferred embodiment of a focusing and dispensing device according to the present invention will now be described with reference to FIGS. 1B, 3A, and 3B. A fluidic microchip 60 has a first focusing channel 84, a sample channel 82, a sample-waste channel 76, buffer channel 74, a collection channel 78, and a chamber 86 which are formed and disposed on a substrate in the same manner as the embodiment described above. Each of the aforementioned respective channels is in fluid communication with the respective reservoir in the same manner as the first embodiment. However, the fluidic microchip 60 also has a second focusing reservoir 68 and a second focusing channel 80, which is in fluid communication with the chamber 86. The chamber 86 is defined by a focusing element 88 and a valving element 90. The focusing channels 80, 84 intersect with the sample channel 82 to form the focusing element 88. The sample channel 82, sample-waste channel 76, buffer channel 74, and collection channel 78 intersect to form the valving element 90.

In the operation of the fluidic microchip device 60, the sample fluid is infused through the focusing chamber 86. The electric potentials at the reservoirs are adjusted to increase or diminish the degree of lateral focusing. The potentials applied at the sample and focusing reservoirs are controlled independently, and the sample-waste reservoir 64 is preferably grounded. Small variations in channel lengths and widths may require that the voltages applied to the reservoirs differ slightly for balancing the field strengths to obtain desired fluid transport in the chamber 86. Assuming that the operational conditions, e.g., relative conductivities of the buffers, applied voltages, electroosmotic transport, remain unchanged, the variability of the stream width over time remains essentially constant.

Focusing of the sample material stream from sample channel 82 occurs with the transport of focusing fluid into the focusing element 88 from the focusing channels 80 and 84 and the transport of sample fluid into focusing chamber 86 from sample channel 82. When the fluid flow rates in each focusing channel 80 and 84 are equal, the sample material stream is confined substantially along the center axis of the sample channel 82. The position of sample material stream within the sample channel 82 may be controlled by adjusting the ratio of fluid flow rates between the two focusing channels 80 and 84. If the focusing flow is too large, the sample is not transported from the sample reservoir 20 to the chamber 86. In FIG. 3A, the arrows depict flow directions in the various channels during focusing.

Figure 3B:
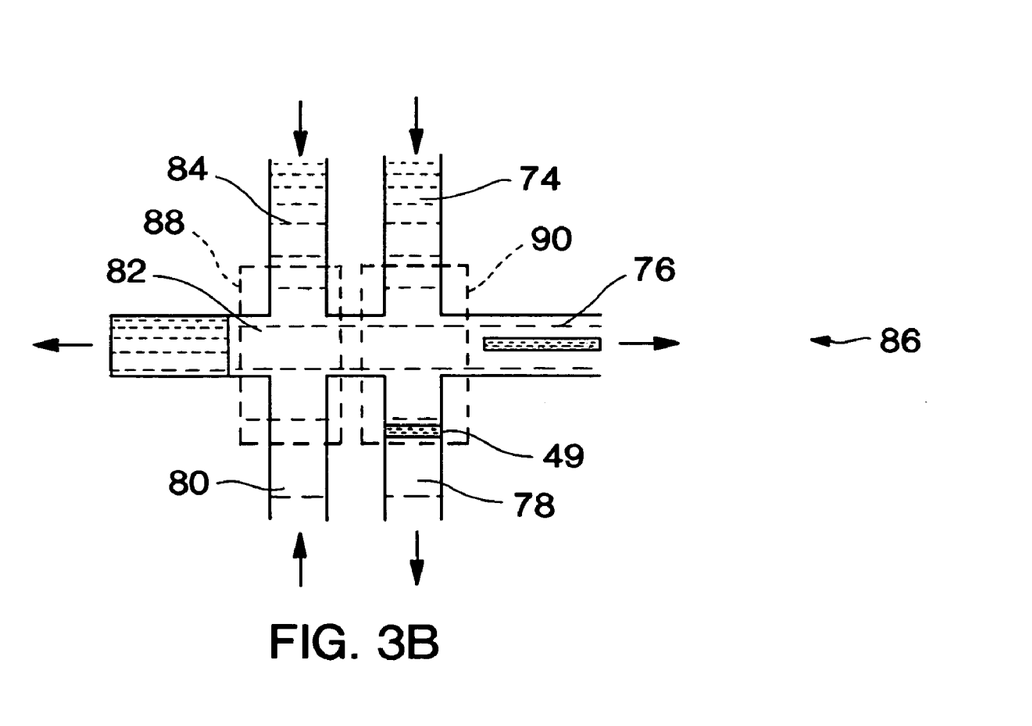

Dispensing of a volume segment of the focused sample material stream from chamber 86 is shown in FIG. 3B and proceeds in a similar manner to the dispensing process using in the embodiment depicted in of FIG. 2B. In FIG. 3B, the arrows depict flow directions in the various channels during dispensing.

Working Example

Figure 1B:
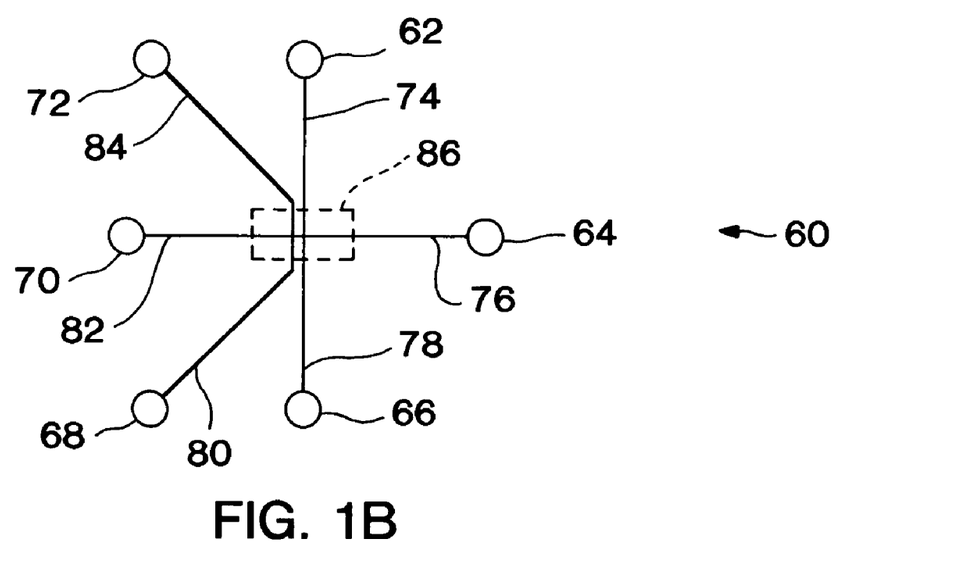
FIG. 1B is a schematic diagram of a fluidic microchip channel network for spatially focusing sample material streams in accordance with a second embodiment of the present invention.
Figure 5A:
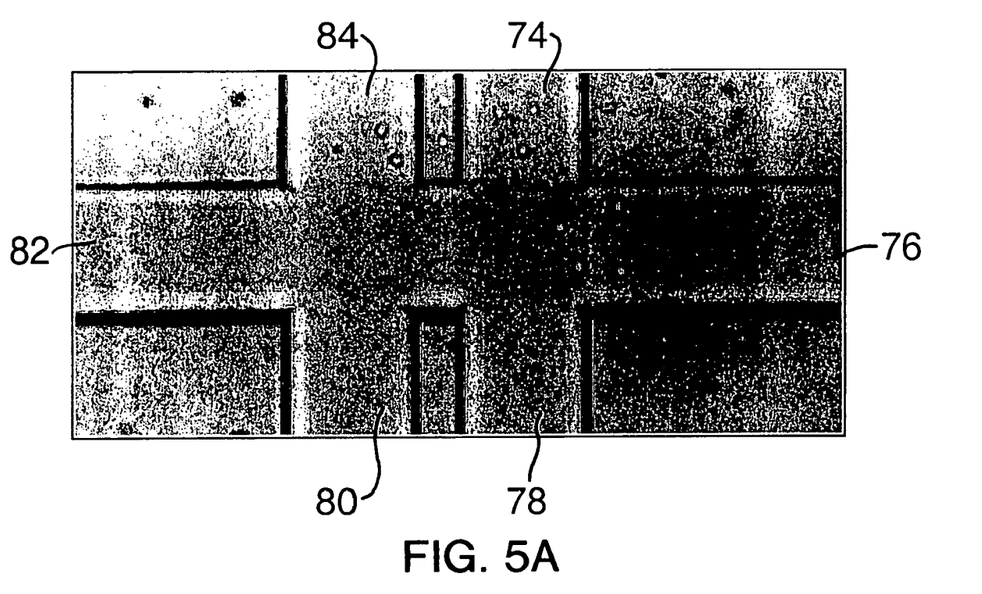
FIG. 5A is a white light image of a chamber used in a fluidic microchip according to the present invention as depicted schematically in FIG. 1B.

In order to demonstrate the functionality of the apparatus and process according to the present invention, a microchannel device having a microchannel network as shown schematically in FIG. 1B was fabricated. FIG. 5A shows a white light image of the chamber 86 schematically depicted in FIGS. 1B, 3A, and 3B with sample channel 82, focusing channels 80 and 84, buffer channel 74, collection channel 78, and sample-waste channel 76. In the device shown in FIG. 5A the channels are 9.0 µm deep and 42 µm wide. The buffer channel 74 and first focusing channel 84 are separated by 14.5 µm. The channel lengths, in millimeters (mm), for this microchip device are listed in Table 1 below. The electroosmotic flow in this experiment is that of native glass.

TABLE 1

| Channel | Length |
| --- | --- |
| 74 | 14.8 |
| 76 | 3.9 |
| 78 | 15.6 |
| 80 | 15.9 |
| 82 | 6.2 |
| 84 | 16.0 |

Figure 5B:
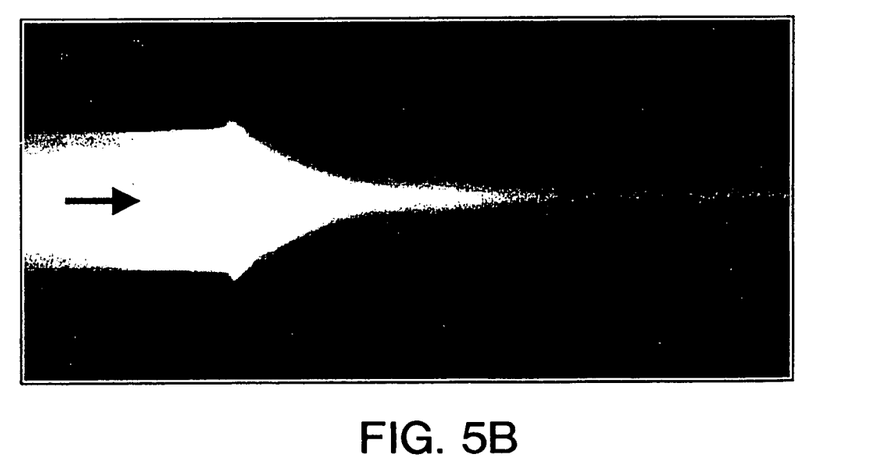
FIG. 5B is a fluorescence image of the chamber of FIG. 5A showing the focusing of a fluid stream therein.

Focusing on the sample material stream is shown in the fluorescence image in FIG. 5B. Rhodamine B in sodium tetraborate buffer is the sample and sodium tetraborate buffer is the buffer and focusing fluid. Focusing of the sample material stream from sample channel 82 occurs with the flow of focusing fluid into the chamber 86 from the focusing channels 80 and 84 and sample fluid into the chamber 86 from sample channel 82. The fluid flow rates in focusing channels 80 and 84 are approximately equal, and the sample material stream is confined substantially along the center axis of the chamber 86. In FIG. 5B, arrows depict direction of flow in chamber 86. The fluid flow from the buffer channel 74 and the collection channel 78 during focusing helps expand, maintain, or further confine the sample stream depending on the potential applied to the respective reservoirs 62 and 66. Set forth In Table 2 are the electric potentials in kilovolts (kv) applied to the reservoirs during focusing of the sample fluid (Focusing) and dispensing of a volume segment of the sample fluid (Dispensing).

TABLE 2

| Reservoir | Focusing | Dispensing |
| --- | --- | --- |
| 62 | 1.9 | 1.9 |
| 64 | 0 | 0.38 |
| 66 | 1.9 | 0 |
| 68 | 1.9 | 0.38 |
| 70 | 1.3 | 0.38 |
| 72 | 1.9 | 0.38 |

To obtain a narrower sample stream width, higher potentials can be applied to the focusing reservoirs 68 and 72 relative to the potential at the sample reservoir 70. Similarly, higher potentials can be also applied to the buffer reservoir 62 and waste reservoir 66 relative to the potential at the sample reservoir 70. Adjustments of the electric potentials at the focusing reservoirs 68 and 72, buffer reservoir 62, and waste reservoir 66 can also be made simultaneously to adjust the stream width. Conversely, lower potentials relative to the potential at the sample reservoir 70 will result in a wider sample stream. FIG. 6 shows the integrated profile of a portion of the segment 49 of the sample stream after being dispensed into the collection channel 78. The profile was detected 0.1 mm downstream from the chamber in the collection channel 78 with laser induced fluorescence.

Microfabricated devices in accordance with the present invention have been described. The devices employ focusing for spatially confining a stream of sample material passing therethrough. The device further employs transport of fluidic material to segment and dispense a portion of the focused sample material stream. The combination of focusing and dispensing is novel. In this way, the microfabricated device is capable of delivering precise, minute volumes of fluidic material reproducibly, by adjusting the axial extent of the dispensed plug. The device of the present invention is advantageous for use in various analytical procedures such as chemical separations. The spatial confinement of the sample fluid in and dispensing of controlled minute volumes from the chamber allows high efficiency, high sample throughput. Also, a microfluidic device in accordance with this invention can be operated with any combination of electrokinetic transport and pressure-driven flow to achieve comparable results.

The terms and expressions which have been employed are used as terms of description and not of limitation. There is no intention in the use of such terms and expressions of excluding any equivalents of the features shown and described or portions thereof. It is recognized, however, that various modifications such as channel dimension, location, and arrangement are possible within the scope of the invention as claimed.

What is claimed is:

1. A method of forming and dispensing minute volume segments of a material in a microfluidic device, said method comprising the steps of:

providing a microfluidic device that includes a body having first, second, third, and fourth microchannels formed therein, said first, second, third, and fourth microchannels communicating at a first intersection and said first microchannel being connected to a source of a first material;

providing a first focusing channel in said body having one end in fluid communication with a source of a focusing material and a second end in fluid communication with said first channel between said source of the first material and the first intersection;

transporting a stream of the first material through said first channel toward the first intersection, said stream of first material having a width;

transporting a stream of the focusing material from the first focusing channel into said first channel, such that the width of the stream of first material in said first channel is narrowed; and dispensing a volume segment of the narrowed first material stream into the fourth channel.

2. A method as set forth in claim 1 comprising the step of transporting a buffer material in said third and fourth channels such that said buffer material acts on said narrowed stream of the first material.

3. A method as set forth in claim 1 or 2 further comprising the steps of:

providing a second focusing channel in said body having one end in fluid communication with a source of focusing material and a second end in fluid communication with said first channel between the source of the first material and the first intersection; and transporting a second stream of the focusing material from the second focusing channel into said first channel such that the width of the stream of the first material in said first channel is narrowed.

4. A method as set forth in claim 3 wherein the step of dispensing the volume segment of the narrowed first material stream into the fourth channel comprises the steps of:

transporting buffer material through said third channel toward the first intersection; and transporting the volume segment of the narrowed first material stream through the fourth channel.

5. A method as set forth in claim 4 which further comprises the step of reversing the direction of the transporting of the stream of the first material in the first channel.

6. A method as set forth in claim 3 wherein the step of transporting the second stream of the focusing material comprises transporting the second stream of the focusing material from the focusing channel into the first channel such that the width of the stream of the first material in the first channel is narrowed substantially along the center axis of the first channel.

7. A method as set forth in claim 2 wherein the step of transporting the buffer material in the third and fourth channels comprises the step of controlling the flow of the buffer material in the third and fourth channels such that the buffer material expands, maintains, or further confines the stream of first material.

8. A method as set forth in claim 1 wherein the step of dispensing the volume segment of the narrowed first material stream into the fourth channel comprises the steps of:
   transporting a first buffer material through said third channel toward the first intersection; and
   transporting the volume segment of the narrowed first material stream through the fourth channel.

9. A method as set forth in claim 8 which further comprises the step of reversing the direction of the transporting of the stream of the first material in the first channel.

10. An apparatus for forming and dispensing minute volume segments of a material in a microfluidic device, the apparatus comprising:
   a substrate having first, second, third, and fourth microchannels formed therein, said microchannels communicating at a first intersection and said first microchannel being connected to a source of a first material;
   a focusing channel formed in said substrate and having one end in fluid communication with a source of a focusing material and a second end in fluid communication with said first channel between said source of the first material and the first intersection;
   means for transporting a stream of the first material through said first channel toward said first intersection, said stream of first material having a width;
   means for transporting a stream of the focusing material into said first channel, whereby the width of the stream of first material in said first channel is narrowed; and
   means for dispensing a volume segment of the narrowed first material stream into the fourth channel.

11. An apparatus as set forth in claim 10 further comprising means for transporting a buffer material in said third and fourth channels such that said buffer material acts on said narrowed stream of the first material.

12. An apparatus as set forth in claim 10 or 11 further comprising:
   a second focusing channel in said body having one end in fluid communication with a source of focusing material and a second end in fluid communication with said first channel between the source of the first material and the first intersection; and
   means for transporting a second stream of the focusing material from the second focusing channel into said first channel such that the width of the stream of the first material in said first channel is narrowed.

13. An apparatus as set forth in claim 12 wherein the means for transporting the stream of the first material, the means for transporting the stream of focusing material, the means for transporting the buffer material, and the means for transporting the second stream of focusing material comprise a means selected from the group consisting of electrokinetic means for effecting the transporting of the respective materials, pressure driven means for effecting the transporting of the respective materials, and a combination thereof.

14. An apparatus as set forth in claim 12 wherein the means for transporting the second stream of the focusing material comprises means for transporting the second stream of the focusing material from the focusing channel into the first channel such that the width of the stream of the first material in the first channel is narrowed substantially along the center axis of the first channel.

15. An apparatus as set forth in claim 11 wherein the means for transporting the stream of the first material, the means for transporting the stream of the focusing material, and the means for transporting the buffer material comprise a means selected from the group consisting of electrokinetic means for effecting the transporting of the respective materials, pressure-driven means for effecting the transporting of the respective materials, and a combination thereof.

16. An apparatus as set forth in claim 10 wherein the means for dispensing the volume segment of the narrowed first material stream into the fourth channel comprises:
   means for transporting a buffer material through said third channel toward the first intersection; and
   means for transporting the volume segment of the narrowed first material stream through the fourth channel.

17. An apparatus as set forth in claim 16 wherein the means for transporting the stream of the first material, the means for transporting the stream of focusing material, the means for transporting the buffer material, and the means for transporting the volume segment of the narrowed first material comprise a means selected from the group consisting of electrokinetic means for effecting the transporting of the respective materials, pressure driven means for effecting the transporting of the respective materials, and a combination thereof.

18. An apparatus as set forth in claim 16 which further comprises means for reversing the direction of the transporting of the stream of the first material in the first channel.

19. An apparatus as set forth in claim 10 wherein the means for transporting the stream of the first material and the means for transporting the stream of the focusing material comprise a means selected from the group consisting of electrokinetic means for effecting the transporting of the respective materials, pressure-driven means for effecting the transporting of the respective materials, and a combination thereof.

* * * * *